(12) United States Patent
Van Tienen

(10) Patent No.: US 10,076,417 B2
(45) Date of Patent: Sep. 18, 2018

(54) JOINT PROSTHESIS ASSEMBLY

(71) Applicant: Stichting Katholieke Universiteit, Nijmegen (NL)

(72) Inventor: Tony George Van Tienen, Nijmegen (NL)

(73) Assignee: ATRO MEDICAL B.V., Nijmegen (NL)

( * ) Notice: Subject to any disclaimer, the term of this patent is extended or adjusted under 35 U.S.C. 154(b) by 11 days.

(21) Appl. No.: 15/028,042

(22) PCT Filed: Jan. 27, 2014

(86) PCT No.: PCT/NL2014/050041
§ 371 (c)(1),
(2) Date: Apr. 8, 2016

(87) PCT Pub. No.: WO2015/057056
PCT Pub. Date: Apr. 23, 2015

(65) Prior Publication Data
US 2016/0235538 A1 Aug. 18, 2016

(30) Foreign Application Priority Data

Oct. 15, 2013 (EP) .................................... 13188641

(51) Int. Cl.
*A61F 2/30* (2006.01)
*A61B 17/56* (2006.01)
*A61F 2/38* (2006.01)

(52) U.S. Cl.
CPC ........ *A61F 2/30756* (2013.01); *A61B 17/562* (2013.01); *A61F 2/30* (2013.01); *A61F 2/3872* (2013.01); *A61F 2220/0008* (2013.01)

(58) Field of Classification Search
CPC ................ A61F 2/30756; A61F 2/3872; A61F 2002/30462; A61F 2002/30464;
(Continued)

(56) References Cited

U.S. PATENT DOCUMENTS 2,765,787 A * 10/1956 Pellet ........................ A61F 2/32
606/64
5,282,867 A * 2/1994 Mikhail ................ A61F 2/0811
623/13.12
(Continued)

FOREIGN PATENT DOCUMENTS

WO 2011138045 11/2011
WO 2012168715 12/2012

OTHER PUBLICATIONS

International Search Report PCT/NL2014/050041 dated Mar. 25, 2014.
(Continued)

*Primary Examiner* — Thomas J Sweet
*Assistant Examiner* — Megan Wolf
(74) *Attorney, Agent, or Firm* — Young & Thompson

(57) ABSTRACT

A joint prosthesis assembly, includes a joint prosthesis body (1) made of a first biocompatible non-resorbable material and an anchoring element (2-5) made of a second biocompatible non-resorbable material. The anchoring element (2-5) is arranged to allow rotation of an end portion of the joint prosthesis body (1) with respect to the anchoring element (2-5) when in situ.

12 Claims, 4 Drawing Sheets

(58) Field of Classification Search
CPC .. A61F 2002/30469; A61F 2002/30757; A61F 2/3868; A61F 2002/30761; A61F 2002/3877
See application file for complete search history.

(56) References Cited

U.S. PATENT DOCUMENTS

| | | | |
|---|---|---|---|
| 7,485,149 B1* | 2/2009 | White | A61F 2/385 606/105 |
| 9,675,387 B2* | 6/2017 | Blain | A61F 2/442 |
| 2002/0107576 A1 | 8/2002 | Meyers et al. | |
| 2004/0167630 A1* | 8/2004 | Rolston | A61F 2/38 623/20.14 |
| 2005/0143745 A1* | 6/2005 | Hodorek | A61B 17/1659 606/87 |
| 2009/0076605 A1 | 3/2009 | Linares | |
| 2012/0203286 A1* | 8/2012 | Armstrong | A61B 17/866 606/304 |

OTHER PUBLICATIONS

International Preliminary Report on Patentability PCT/NL2014/050041 dated Jan. 29, 2016.

* cited by examiner

JOINT PROSTHESIS ASSEMBLY

FIELD OF THE INVENTION

The present invention relates to a joint prosthesis assembly, e.g. meant for interposition between bone-bone, cartilage-cartilage and soft tissue surfaces such as a meniscus prosthesis assembly for a human or animal (knee) joint. More in particular, the present invention relates to a joint prosthesis assembly, comprising a joint prosthesis body made of a first biocompatible non-resorbable material.

PRIOR ART

International patent publication WO2011/138045 discloses a non-resorbable meniscus prosthesis for the human knee joint, having two end plugs and a polymer cord attached to each of the end plugs.

SUMMARY OF THE INVENTION

The present invention seeks to provide an improved joint prosthesis assembly, such as a meniscus prosthesis assembly, allowing durable fixation of the prosthesis even under prolonged in-situ use including rotational and other stresses.

According to the present invention, a joint prosthesis assembly according to the preamble defined above is provided, further comprising an anchoring element made of a second biocompatible non-resorbable material, wherein the anchoring element is arranged to allow rotation of an end portion of the joint prosthesis body with respect to the anchoring element when in situ. This provides for a non-rigid fixation of the prosthesis body. Further embodiments are described in the claims as attached. The present invention embodiments provide a long-lasting fixation of the horns (i.e. the ends of the joint prosthesis body in the case of a meniscus implant) to the tibial plateau and attachment of biomaterials to a joint in general.

SHORT DESCRIPTION OF DRAWINGS

The present invention will be discussed in more detail below, using a number of exemplary embodiments, with reference to the attached drawings, in which FIG. 1a shows a cross sectional view of a joint prosthesis assembly according to an embodiment of the present invention, when in situ in a knee joint;

Figure 4:
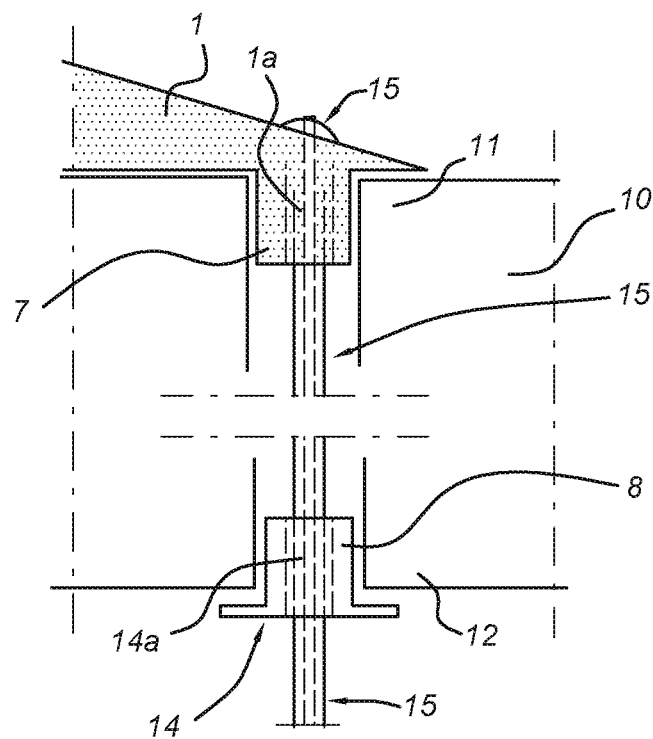

FIG. 2a-d show top and side views of a part of the joint prosthesis assembly embodiment of FIG. 1a-d;

FIG. 3a-f show perspective views of various alternative embodiments of the joint prosthesis assembly according to the present invention;

FIG. 4 shows a cross sectional view of yet a further embodiment of the joint prosthesis assembly according to the present invention.

DETAILED DESCRIPTION OF EXEMPLARY EMBODIMENTS

The present invention embodiments are a contribution to the long durability of an implant and the ease of the implantation technique. The features of the present invention embodiments may also be applied in further implantation applications other than knee implants, as discussed mainly in the embodiments described below with reference to the drawings, such as shoulder and spine implants. Thus, the present invention may also apply to a joint prosthesis assembly, comprising a joint prosthesis body made of a first biocompatible non-resorbable material; an anchoring element made of a second biocompatible non-resorbable material; wherein the anchoring element is arranged to allow rotation of an end portion of the joint prosthesis body with respect to the anchoring element when in situ. The present invention embodiments solve the difficulty of creating a long-lasting fixation of the horns to the tibial plateau and attachment of biomaterials to a joint in general.

In the following description several ways of horn fixation are disclosed involving a meniscus prosthesis assembly, but which may work for other implants in other joints as well.

Figure 1A:
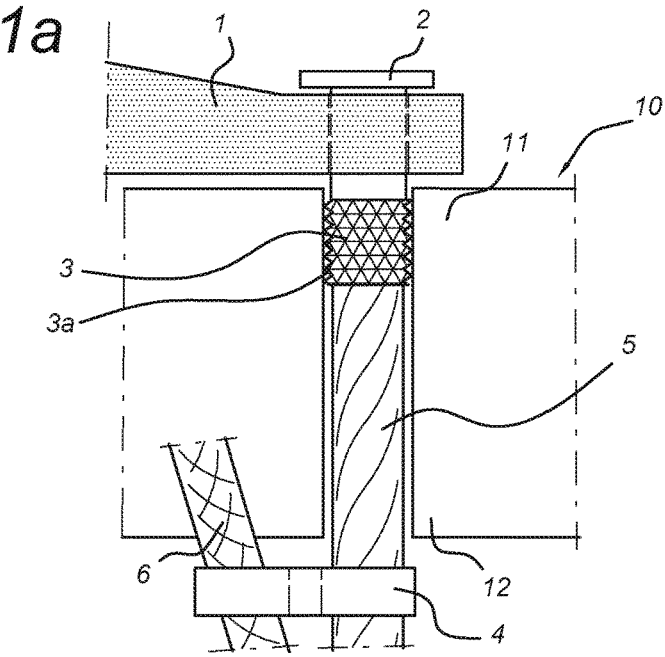
FIG. 1b shows a more general front view of a joint wherein the joint prosthesis is applied.
FIG. 1c shows a perspective view of a joint prosthesis in an embodiment as meniscus prosthesis.
FIG. 1d shows a perspective view of a joint prosthesis in the form of a meniscus prosthesis positioned on a tibia.
Figure 1B:
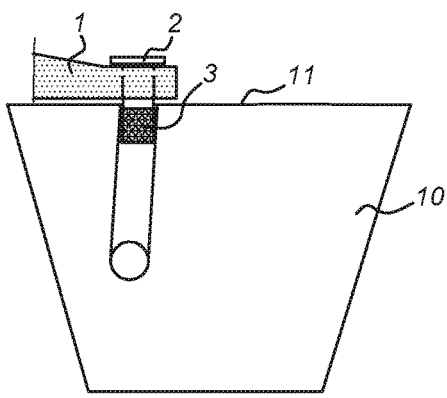
Figure 1C:
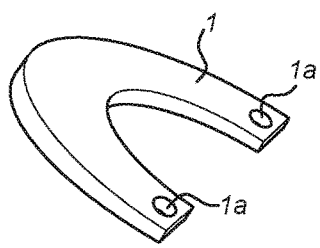
Figure 1D:
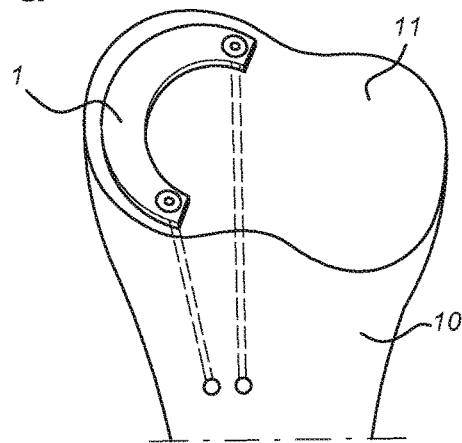
Figure 2A:
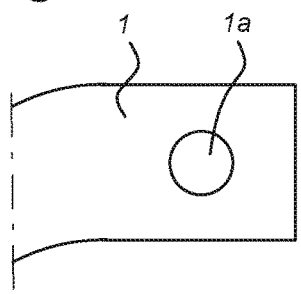
Figure 2B:
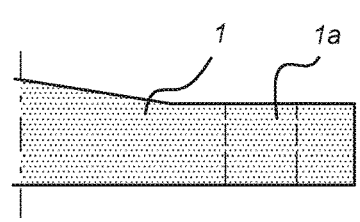
Figure 2C:
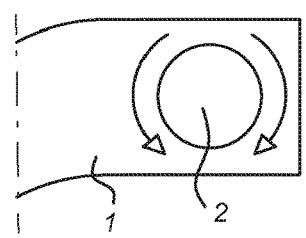
Figure 2D:
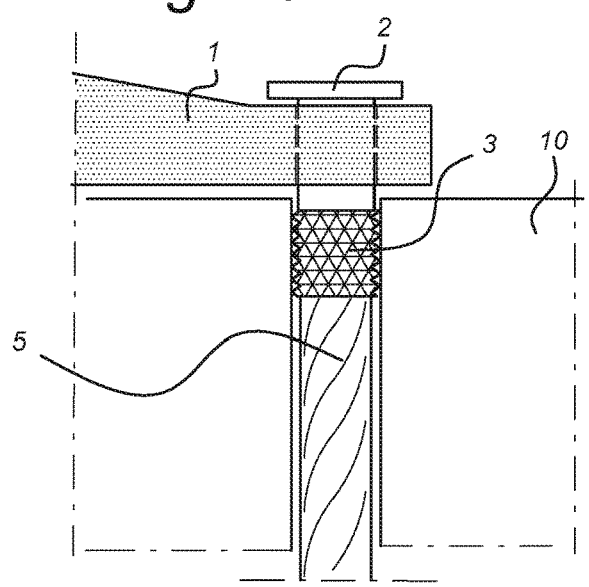

FIG. 1a shows a cross sectional view of a joint prosthesis assembly according to an embodiment of the present invention, when in situ in a knee joint. FIG. 1b shows a more general view of a joint wherein the joint prosthesis is applied. FIG. 1c shows a perspective view of a joint prosthesis, more in particular a meniscus prosthesis. In FIG. 1d, a perspective is shown of a meniscus implant positioned on a tibia bone. The bone of the tibia is only shown schematically as tibia bone 10, having a tibial plateau 11 and a lower (antero medial) side 12 of the tibia on both ends of the drill tunnel. In FIG. 1a, a part of the meniscus prosthesis body 1 on one end thereof is shown, where the prosthesis body 1 is fixated to the underlying surface, e.g. a tibia plateau 11 of a knee joint.

In patent publication WO2011/138045, fixation of the meniscus implant to the underlying tibia plateau occurs with sutures or polymer cords through the horns which run further into drill holes provided in the tibia. These cords are responsible to maintain the horns of the implant in a stable position on the tibial plateau while the rest of the implant moves with the movement of the knee joint. While the implant does not biologically integrate into the surrounding tissue, it completely and infinitely relies on the horn attachments to the tibia, i.e. the polymer cords. Although the cords are strong, rubbing against the bone will probably break the polymer material and the implant becomes a loose body in the joint with no function. The fixation depends on the strength of the polymer cords.

The surgical procedure for using a joint prosthesis assembly according to the present invention embodiments is as follows. Under guidance of arthroscopic view the exact anatomic position of the anterior and posterior attachment of the meniscus are determined. With an aiming device a hole is drilled from a more distal location on the anterior side of the tibia in the direction of the anatomic meniscus horn attachments in the joint. In this way two drill holes in divergent directions are created in which the cords/cables (5 and 6 in FIGS. 1a and 1b) are pulled which again pull the meniscus implant in the joint.

FIGS. 1a and 1b show a present invention embodiment of a joint prosthesis assembly, comprising a joint prosthesis body 1 and an anchoring element 2-6. FIGS. 2a-2d show various top and side views of a part of the joint prosthesis body 1 alone, or in combination with further elements. In this embodiment, the anchoring element comprises a plug 3 with a disc shaped end 2, attached to a (metal or polymer) cable 5, which runs through a drill hole in the tibia plateau 11 and is fixated with a component at the other end of the drill hole, e.g. using a cable clamp 4. The plug 3 is held in an aperture 1a (or bore 1a) of the prosthesis body 1 using the disc or conus shaped end 2 (see also the various views of FIGS. 2a-d: the disc shaped end 2 may rest on top of the prosthesis body 1, or sink (partly) into the prosthesis body 1). As shown partly in FIG. 1, the other end of the meniscus prosthesis body 1 (at the posterior horn) is kept in its position on the posterior attachment of the tibia 10, using a second cable 6, in a separate drill hole through the tibia. In case of use of metal cables 5, 6, the cable clamp 4 is then suited to clamp the two cables 5, 6 using a single component. When a polymer cord is used for cables 5, 6, other techniques or devices may be used to fixate the cables 5, 6 to each other or to the outer end of the tibia (e.g. knotting the cords/cables 5, 6 to each other, interference screws). The concept of the plug-cable fixation as shown allows the implant (i.e. the end of the prosthesis body 1) to rotate around the smooth (metal) plug 3. To ensure that the implant 1 rotates around the plug 3 and not the plug 3 in the drill hole, the plug 3 can be textured with a surface layer 3a (see FIG. 1a, for example hydroxy apatite or tri-calcium phosphate, metal granules or variants) to allow ingrowth in the surrounding bone of the tibia 10. In this way the risk of tunnel widening is also reduced.

The joint prosthesis body 1 made of a first biocompatible non-resorbable material, and the anchoring element (2-6) or its components are made of a second biocompatible non-resorbable material. The first and second biocompatible non-resorbable material may be the same or similar, or different.

The components of the anchoring element 2-6 can be of a single material, such as stainless steel, or another biocompatible metal or biocompatible material, or can be of different materials. The polymer of the joint prosthesis body 1 is e.g. chosen to glide smoothly around the post (i.e. surface of the plug 3). The concept of metal-on-plastic motion is a proven concept in total joint prostheses, although the gliding characteristics of the implant depend on the polymer used, however, other biocompatible materials are also possible.

It is technically demanding to develop a meniscus horn on the existing implant 1, in one piece, which slowly integrates with the bone of the tibia plateau 11, as the implant described in the prior art publication WO2011/138045. Furthermore, the forces during movement of the knee are the highest at the transition implant-tibia and so are the chances on breakage of the implant 1.

The advantage of the present embodiments is that the implant or joint prosthesis body 1 is allowed to rotate around the (metal or other material) plug 3 in the drill hole, or in other words, the anchoring element 2-5 is arranged to allow rotation of an end portion of the joint prosthesis body 1 with respect to the anchoring element 2-5 when in situ. In this way the forces on the implant 1 are reduced and will increase the durability of the fixation and implant 1.

The lower end of the (metal) plug 3 (i.e. surface 3a as indicated in FIG. 1) can be spray coated with a bone ingrowth enhancing layer (e.g. Hydroxy-apatite, Tri-calcium-phosphate, metal granules). In a further alternative embodiment, the (metal) plug 3 comprises a textured surface 3a. This part provides the fixation to the tibia 10, while the disc-shaped part 2 of the embodiment of FIGS. 1 and 2 holds the joint prosthesis 1 in its correct position, yet allowing rotation of the joint prosthesis 1.

The implant 1 comprises one or two part components. In an embodiment, the implant 1 comes in one, single, integrated piece. The material with the through hole will have to be suitable to sustain the forces exercised on the implant 1 while having been implanted, and in daily activity.

Figure 3A:
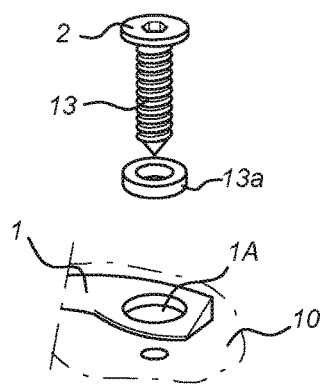
Figure 3B:
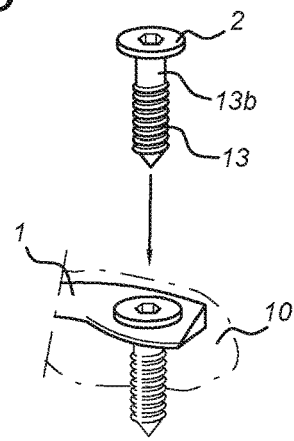

Alternative embodiments for the joint prosthesis assembly are shown in the perspective views of FIG. 3a-3f:

The same meniscus implant form (joint prosthesis body 1) with a hole 1a for a plug 3 and the implant rotates around the plug 3 (i.e. the part without thread). The plug 3 is anchored in the tibia plateau 10 by a screw thread 13 on an end part of the plug 3, as shown in the embodiments of FIGS. 3a and 3b. The disc 2, plug 3 and screw thread 13 shown in the embodiments of FIGS. 3a and 3b together form a screw which can be handled using known tools. This screw tread 13 may be coated with bone ingrowth enhancing materials (hydroxy apatite or tri-calcium phosphate, metal granules or variants). Note that part of the plug 3 may be void of a screw thread, allowing the prosthesis part 1 to rotate freely with respect to the plug 3 analog to the cable plug system as described above.

FIG. 3a shows an embodiment, where an additional cylindrical body 13a positioned in the bore 1a of the prosthesis body 1 is used to allow relative rotation between prosthesis body 1 and tibia 10. The cylindrical body 13a is fixed to the tibia plateau 11 by the screw thread 13, and its outer surface is congruent to the inner surface of the bore 1a. FIG. 3b shows an alternative requiring one part less, wherein a top part 13b of the plug 3 is void of the screw thread 13 and aligns with the bore 1a inner surface to allow mutual rotation.

Figure 3C:
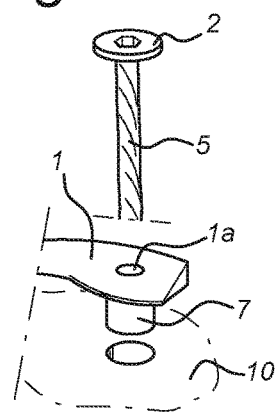
Figure 3D:
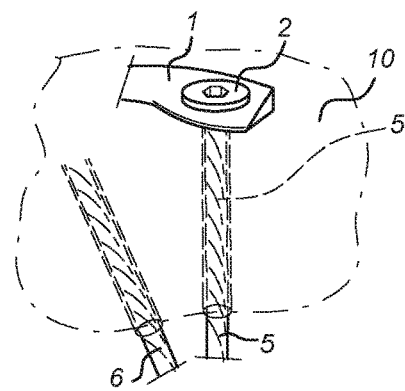

FIGS. 3c and 3d show a further embodiment, wherein the joint prosthesis body 1 comprises at least one primary bone plug 7 having a bore 1a there through (at the end of the prosthesis body 1. The at least one primary bone plug 7 has a shape adapted to fit the drill hole in the tibia 10, yet allowing relative rotation. The anchoring element 2-6 in this embodiment comprises a (metal) disc 2 and a polymer cord 5 as cable directly attached to the disc 2. In other words, the same meniscus implant form is used with a hole 1a for a polymer cord 5 and an integrated plug in the form of the disc 2 in the implant 1. As shown in FIG. 3d, the polymer cord 5 (and similar polymer cord 6 originating from the posterior tibia) exit from the drill holes in the tibia, and can be fixated in a regular manner (e.g. tying the two cords 5, 6, or fixating the cords 5, 6 at the exit of the respective drill holes at the outer end of the tibia 10, e.g. using other techniques or devices (e.g. an interference screw)).

Figure 3E:
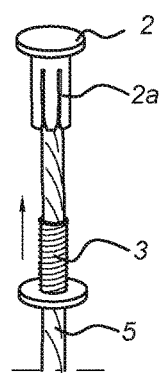
Figure 3F:
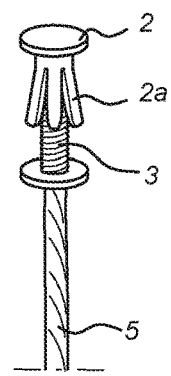

An even further alternative embodiment is shown in FIGS. 3e and 3f. The cable 5 and plug 3 are somewhat similar to the previous embodiment, however the plug 3 is now an integrated anchoring system in the form of an anchoring screw 2, 2a, 3 attached to the cable 5. It is noted that the concept of anchoring screw 2, 2a, 3 as such is known: the top part 2 being provided with extendable tabs 2a, which are forced outward when screwing on the lower part 3.

In FIG. 4 a further embodiment is shown in a cross sectional view. At least one primary bone plug 7 is provided as part of the prosthesis body 1, intended for insertion in a hole provided in a bone part of a joint, such as the drilled hole in the tibia 10 as shown in FIG. 4.

The primary bone plug 7 is made of a fourth biocompatible non-resorbable material, and is in engagement with an end portion of the meniscus prosthesis body 1 when in situ. The anchoring element 2-5 further comprises at least one secondary bone plug 14 made of a fifth biocompatible non-resorbable material, and at least one connecting element 15, e.g. a polymer cord or metal cable, attaching the at least one primary bone plug 7 and the at least one secondary bone plug 14 when in situ. In other words, a variant is provided with an integrated plug (or primary bone plug 7) in implant 1 with polymer or metal cords 15 through the plug 7 and a plug (or secondary bone plug 14) at the surface 12 of the anterior tibial bone. In a further embodiment the at least one primary bone plug 7 and the at least one secondary bone plug 14 each comprise a bone insertion end having an outer diameter larger than an outer diameter of the at least one connecting element 5, allowing free rotation at interfaces between the joint prosthesis body 1 and the tibia 10. The at least one primary bone plug 7 and the joint prosthesis body 1 are integrally formed as a single piece component in an even further embodiment.

For the embodiments described herein, the (metal) plug 3 with the (steel) cable 5 (or the alternative embodiments of the anchoring element 2-5) provides a stable fixation in the bone 10 and the implant horn 7 can rotate freely around the plug 3. This reduces the forces on the implant 1 and the chance on breakage of the implant 1.

The novelty of the joint prosthesis assembly according to the FIGS. 1 and 2a-2d embodiments is the combination of the cable wire 5 with the plug 3 (plus optionally the surface texture 3a for fixation to the bone 10). By fixating metal (or other plug material) to the bone 10 and not the implant polymer 1 itself reduces the rotational forces on the polymer material of the implant 1. The advantage is that the shear forces on the implant 1 are translated to another material than the material of the implant 1 itself, which provides a freedom to choose for better suitable materials. In some of the embodiments as shown, the plug 3 is longer than the thickness of the horn 7 of the implant 1, (it extends past the edge of the bone 10), such that a cable/polymer cord 5, 15 attached to the plug 3 does not come into contact with the edge of the bone 10.

It is noted that combinations of the embodiments may be used, e.g. in knee implants 1 the back horn can be fixed using one of the cable embodiments, and the front horn using the screw embodiment.

In the embodiments disclosed, the horns of the biocompatible non-resorbable material, i.e. the end portion of the joint prosthesis body 1, need to sustain forces in between 100 and 1000N, or even more without deformation or tearing of the biocompatible material. The number of 100-1000N represents the pulling force on the horns of the meniscus implant during normal physiologic loading, and may be achieved by using a suitable biocompatible non-resorbable material and dimensions of the joint prosthesis body 1.

In some embodiments the biocompatible non-resorbable material comprises a polymer. Preferably, the meniscus prosthesis body of the meniscus prosthesis assembly according to the present invention is made of a biocompatible polymeric material. In some embodiments the biocompatible polymeric material is selected from the group comprising a hydrogel material (such as a synthetic polyacrylonitrile polymer, PVA hydrogel), elastomers, polypropylene, polyethylene, PEEK, silicon rubbers, and polyurethane carbonates, like for example trimethyl carbonate polyurethane. Preferably silicon rubbers or polyurethane carbonates are used. Such materials together with the design of the meniscus prosthesis body provide the required properties to the meniscus prosthesis body, e.g. high tear strength, high strain at break, flexibility, high stiffness, high wear resistance. Other examples of suitable biocompatible materials can be natural materials, such as collagen, tendon or fibro cartilage. Combinations of polymeric materials can also be used. Obviously the horns of a meniscus prosthesis transfer the forces from the implant to fixation sites on the tibia plateau. Due to the high physiologic forces on the horns (i.e. the end portions of the prosthesis body in a meniscus type of the joint prosthesis assembly) reinforcements of prosthesis body and the horns with a second integrated (polymer) material may be applied to withstand these forces. Obviously the horns of the meniscus transfer the forces from the implant body to fixation sites on the tibia plateau. Due to the small diameter of the horns reinforcements of body and the horns with a second integrated (polymer) material may be necessary to withstand these forces.

The implant fixation according to the present invention embodiments makes it an easy implantation technique for the surgeon. A very important goal in the development of meniscus implants is to keep the surgical procedure simple: this addition to the implant makes it applicable for every orthopedic surgeon.

The present invention embodiments have been described above with reference to a number of exemplary embodiments as shown in the drawings. Modifications and alternative implementations of some parts or elements are possible, and are included in the scope of protection as defined in the appended claims.

The invention claimed is:

1. A joint prosthesis assembly, comprising:
a joint prosthesis body made of a first biocompatible non-resorbable material, the joint prosthesis body comprising an end portion having a bore;
an anchoring element comprising a plug made of a second biocompatible non-resorbable material, and a cable attached to the plug, the cable being made of a third biocompatible non-resorbable material,
the plug disposed within and extending through the bore of the end portion and is arranged to allow free rotation of the end portion of the joint prosthesis body with respect to the anchoring element when in situ,
wherein the plug comprises a thread, texture or bone ingrowth enhancing layer configured to secure the plug within a bore in a bone such that the plug is partially disposed within the bone.

2. The joint prosthesis assembly of claim 1, wherein the second biocompatible non-resorbable material of the plug is a high strength material.

3. The joint prosthesis assembly of claim 1, wherein the anchoring element further comprises a cable clamp.

4. The joint prosthesis assembly of claim 1, wherein the joint prosthesis body is configured to replace a native meniscus.

5. The joint prosthesis assembly of claim 1, wherein ends of the joint prosthesis body are arranged to withstand a force of between 100 and 1000N.

6. The joint prosthesis assembly of claim 1, wherein the first biocompatible non-resorbable material comprises a polymer selected from the group consisting of silicon rubbers and polyurethane carbonates.

7. The joint prosthesis assembly of claim 1, wherein the joint prosthesis body is a meniscus prosthesis body and comprises a gliding surface configured for being arranged at an angle with a tibial plateau of between 20° and 45°.

8. The joint prosthesis assembly of claim 1, wherein the cable is formed from stainless steel or polymer.

9. The joint prosthesis assembly of claim 1, wherein the second biocompatible non-resorbable material of the plug is a biocompatible polymer or a metal.

10. The joint prosthesis assembly of claim 1, wherein the plug is coated with a bone ingrowth enhancing layer.

11. The joint prosthesis assembly of claim 1, wherein the plug is coated with a bone ingrowth enhancing layer formed from hydroxyl-apatite, tri-calcium phosphate or metal granules.

12. The joint prosthesis assembly of claim 1,
wherein the plug comprises an integrated anchoring system comprising a top part and a lower part, and
wherein the lower part comprises a thread, and the top part comprises extendable tabs configured to be forced outwardly when screwed onto the threaded lower part.

* * * * *